(12) United States Patent
Armstrong et al.

(10) Patent No.: US 9,839,732 B2
(45) Date of Patent: *Dec. 12, 2017

(54) WIRELESS POWER SYSTEM

(71) Applicant: EVERHEART SYSTEMS INC., Webster, TX (US)

(72) Inventors: Randolph K. Armstrong, Houston, TX (US); Greg S. Aber, Houston, TX (US)

(73) Assignee: EVERHEART SYSTEMS INC., Webster, TX (US)

(*) Notice: Subject to any disclaimer, the term of this patent is extended or adjusted under 35 U.S.C. 154(b) by 247 days.

This patent is subject to a terminal disclaimer.

(21) Appl. No.: 14/537,849

(22) Filed: Nov. 10, 2014

(65) Prior Publication Data
US 2015/0061591 A1    Mar. 5, 2015

Related U.S. Application Data

(63) Continuation of application No. 13/038,671, filed on Mar. 2, 2011, now Pat. No. 8,901,775.
(Continued)

(51) Int. Cl.
*H01F 38/14* (2006.01)
*A61M 1/10* (2006.01)
(Continued)

(52) U.S. Cl.
CPC .......... *A61M 1/1086* (2013.01); *A61M 1/127* (2013.01); *H01F 38/14* (2013.01);
(Continued)

(58) Field of Classification Search
CPC .......... H02J 50/00; H02J 5/005; H01F 38/14; H01F 27/006; H04B 5/0037
(Continued)

(56) References Cited

U.S. PATENT DOCUMENTS 4,785,827 A    11/1988  Fischer
5,290,227 A     3/1994  Pasque
(Continued)

FOREIGN PATENT DOCUMENTS

CA    2209179 A1    7/1996
EP    0714317 A1    6/1996
(Continued)

OTHER PUBLICATIONS

Dixon, L.H., "Eddy Current Losses in Transformer Windings and Circuit Wiring," <http://focus.ti.com/lit/ml/slup197/slup197.pdf>.
(Continued)

*Primary Examiner* — Daniel Kessie
(74) *Attorney, Agent, or Firm* — Nathan S. Smith; Mark I. Bentley; McDermott Will & Emery LLP

(57) ABSTRACT

A wireless power system capable of transmitting power through the skin over distances ranging from a few inches to several feet includes an external transmitting coil assembly and a receiving coil assembly. A transmitting resonant coil and a receiving resonant coil are constructed as to have closely matched or identical resonant frequencies so that the magnetic field produced by the transmitting resonant coil is able to cause the receiving resonant coil to resonate strongly also, even when the distance between the two resonant coils greatly exceeds the largest dimension of either coil. The receiving resonant coil then creates its own local time varying magnetic field, which inductively produces a voltage to provide power to an active implantable medical device or implantable rechargeable battery.

49 Claims, 6 Drawing Sheets

Related U.S. Application Data

(60) Provisional application No. 61/421,779, filed on Dec. 10, 2010.

(51) Int. Cl.
*H02J 7/02* (2016.01)
*A61M 1/12* (2006.01)
*H02J 5/00* (2016.01)

(52) U.S. Cl.
CPC .............. *H02J 5/005* (2013.01); *H02J 7/025* (2013.01); *A61M 1/10* (2013.01); *A61M 1/101* (2013.01); *A61M 1/12* (2013.01); *A61M 1/122* (2014.02); *A61M 2205/8243* (2013.01)

(58) Field of Classification Search
USPC .......................................................... 307/104
See application file for complete search history.

(56) References Cited

U.S. PATENT DOCUMENTS

| | | | |
|---|---|---|---|
| 5,370,509 | A | 12/1994 | Golding et al. |
| 5,702,431 | A | 12/1997 | Wang et al. |
| 6,048,363 | A | 4/2000 | Nagyszalanczy et al. |
| 6,227,797 | B1 | 5/2001 | Watterson et al. |
| 6,234,772 | B1 | 5/2001 | Wampler et al. |
| 6,240,318 | B1 | 5/2001 | Phillips |
| 6,445,956 | B1 | 9/2002 | Laird et al. |
| 6,547,530 | B2 | 4/2003 | Ozaki et al. |
| 6,593,841 | B1 | 7/2003 | Mizoguchi et al. |
| 6,894,456 | B2 | 5/2005 | Tsukamoto et al. |
| 7,616,997 | B2 | 11/2009 | Kieval et al. |
| 7,682,301 | B2 | 3/2010 | Wampler et al. |
| 7,699,586 | B2 | 4/2010 | LaRose et al. |
| 7,741,734 | B2 | 6/2010 | Joannopoulos et al. |
| 7,825,543 | B2 | 11/2010 | Karalis et al. |
| 8,362,651 | B2 | 1/2013 | Hamam et al. |
| 8,551,163 | B2 | 10/2013 | Aber et al. |
| 8,901,775 | B2 | 12/2014 | Armstrong et al. |
| 2003/0091249 | A1 | 5/2003 | Kurimura et al. |
| 2006/0155159 | A1 | 7/2006 | Melvin |
| 2008/0211320 | A1 | 9/2008 | Cook et al. |
| 2008/0269828 | A1 | 10/2008 | Sequeira Abreu |
| 2009/0051224 | A1 | 2/2009 | Cook et al. |
| 2009/0058189 | A1 | 3/2009 | Cook et al. |
| 2009/0058361 | A1 | 3/2009 | John |
| 2009/0072628 | A1 | 3/2009 | Cook et al. |
| 2009/0079268 | A1 | 3/2009 | Cook et al. |
| 2009/0112626 | A1 | 4/2009 | Talbot et al. |
| 2009/0171420 | A1 | 7/2009 | Brown et al. |
| 2009/0224609 | A1 | 9/2009 | Cook et al. |
| 2009/0234447 | A1 | 9/2009 | LaRose et al. |
| 2009/0270679 | A1 | 10/2009 | Hoeg et al. |
| 2010/0045114 | A1 | 2/2010 | Sample et al. |
| 2010/0052811 | A1 | 3/2010 | Smith et al. |
| 2010/0060431 | A1 | 3/2010 | Stevenson et al. |
| 2010/0063347 | A1 | 3/2010 | Yomtov et al. |
| 2010/0102640 | A1 | 4/2010 | Joannopoulos et al. |
| 2010/0102641 | A1 | 4/2010 | Joannopoulos et al. |
| 2010/0109445 | A1 | 5/2010 | Kurs et al. |
| 2010/0117456 | A1 | 5/2010 | Karalis et al. |
| 2010/0133920 | A1 | 6/2010 | Joannopoulos et al. |
| 2010/0164296 | A1 | 7/2010 | Kurs et al. |
| 2010/0184371 | A1 | 7/2010 | Cook et al. |
| 2010/0185280 | A1 | 7/2010 | Ayre et al. |
| 2010/0210233 | A1 | 8/2010 | Cook et al. |
| 2010/0219694 | A1 | 9/2010 | Kurs et al. |
| 2010/0231053 | A1 | 9/2010 | Karalis et al. |
| 2010/0259108 | A1 | 10/2010 | Giler et al. |
| 2010/0277005 | A1 | 11/2010 | Karalis et al. |
| 2010/0305662 | A1 | 12/2010 | Ozawa et al. |
| 2010/0327661 | A1 | 12/2010 | Karalis et al. |
| 2011/0195666 | A1 | 8/2011 | Forsell |
| 2011/0281535 | A1 | 11/2011 | Low et al. |
| 2012/0010079 | A1 | 1/2012 | Sedwick |
| 2012/0032522 | A1 | 2/2012 | Schatz et al. |
| 2012/0089225 | A1 | 4/2012 | Akkerman et al. |
| 2012/0112554 | A1 | 5/2012 | Kim et al. |
| 2012/0119587 | A1 | 5/2012 | Cheon et al. |
| 2012/0139355 | A1 | 6/2012 | Ganem et al. |
| 2012/0146575 | A1 | 6/2012 | Armstrong et al. |
| 2012/0150291 | A1 | 6/2012 | Aber et al. |
| 2012/0153893 | A1 | 6/2012 | Schatz et al. |
| 2013/0241306 | A1 | 9/2013 | Aber et al. |
| 2013/0345493 | A1 | 12/2013 | Aber et al. |
| 2014/0252873 | A1 | 9/2014 | Irish et al. |
| 2014/0255225 | A1 | 9/2014 | Aber et al. |

FOREIGN PATENT DOCUMENTS

| | | |
|---|---|---|
| EP | 1113177 A2 | 7/2001 |
| WO | WO-2009/091267 A2 | 7/2009 |
| WO | WO-2010/042054 A1 | 4/2010 |

OTHER PUBLICATIONS

Kurs, A., "Power Transfer Through Strongly Coupled Resonances," MIT Department of Physics, Master's Thesis, Sep. 2007.

Murgatroyd, et al., "The Frequency Dependence of Resistance in Foilwound Inductors," Electrocomponent Science and Technology 1979, vol. 5, pp. 219-222.

Sample, et al., "Analysis, Experimental Results, and Range Adaptation of Magnetically Coupled Resonators for Wireless Power Transfer," IEEE, 2010.

European Office Action dated Nov. 7, 2016, which issued European Application No. 14159404.4.

Extended European Search Report from European Patent Application No. 17159937.6, dated Jul. 4, 2017.

WIRELESS POWER SYSTEM

RELATED APPLICATIONS

This application is a Continuation of U.S. patent application Ser. No. 13/038,671, filed on Mar. 2, 2011, which claims the benefit of U.S. Provisional Patent Application No. 61/421,779, filed on Dec. 10, 2010, which are incorporated herein by reference.

FIELD OF THE INVENTION

This invention relates to powering devices with wireless energy transfer over short and long distances. More particularly, systems and methods discussed herein are related to powering active implantable medical devices with wireless systems and methods.

BACKGROUND OF INVENTION

Many medical devices require electrical power to operate. Non-limiting examples of such medical devices may include pacemakers, defibrillators, drug infusion pumps, neural stimulators, ventricular assist devices (VAD), and total artificial hearts (TAH). Some devices, such as pacemakers and drug infusion pumps, require such little power that an implanted non-rechargeable battery can last for several years, reducing the need for an implantable rechargeable power source. Other devices, such as some neural stimulators, may require power levels that an implanted non-rechargeable battery cannot supply for more than a few days or weeks. These devices require the use of an implantable rechargeable battery and necessitate recharging every few days or weeks. Other relatively high-power consumption implantable devices, such as VADs and TAHs, may require power levels that an implantable rechargeable battery cannot supply for more than a few hours. With these devices, it may not be feasible to implant additional rechargeable batteries due to the size and space required. As a result, these devices necessitate recharging many times per day or the use of an external rechargeable battery pack.

A common issue encountered by powering or recharging high-power consumption implantable devices, such as VADs or TAHs, is the need for a percutaneous wire that exits the skin to transmit power from an external power source to an implanted battery or directly to the implanted device. This percutaneous wire can be a source of infection, restricts the patient from normal bathing or swimming, and can potentially leave the implanted device without power if it mechanically breaks. Some wireless power transfer systems have been developed that use inductive coupling between an implanted coil and an external coil to transfer power across the skin, thereby obviating the need for a percutaneous wire. This type of wireless power transfer system simply uses the inductive effect between two coils similar to a standard transformer. This approach has been used widely to recharge implanted batteries in some neural stimulators. However, these systems may require precise alignment between the two coils, require close spacing between coils on the order of a few inches or less, can generate significant amounts of heat near the skin, and require the patient to be immobile during charging if the external power source is not easily mobile.

While there is limited use of wireless power systems in some neural stimulators, wide use of wireless power systems for active implantable medical devices has not been adopted. Currently, few applications of wireless power transfer have been applied to VADs or TAHs due to the higher power transfer levels required, relatively high power consumption of such devices, limited space available for implantable rechargeable batteries, limited capacity of implantable rechargeable batteries, and the like. Wireless power transfer systems and methods that can transfer sufficient power required to operate high-power consumption implantable devices while simultaneously recharging implantable batteries are discussed herein. These wireless power transfer systems and methods eliminate percutaneous wires, provide sufficient power for operation and/or charging, provide improvement in the operation and/or charging range, allow the patient to live a more normal lifestyle, provide more patient mobility, and reduce skin heating effects.

SUMMARY OF THE INVENTION

The discussion herein provides a description of a wireless power transfer system intended to recharge implantable batteries, power implantable medical devices, or simultaneously power active implantable medical devices while recharging implantable batteries.

In an illustrative implementation, a wireless power transfer system for implantable medical devices includes a transmitting coil assembly and a receiving coil assembly. The transmitting coil assembly includes an excitation coil and transmitting resonant coil which are inductively coupled to each other and are housed in a durable housing. The receiving coil assembly includes a receiving resonant coil and a power pick-up coil which are also inductively coupled to each other. In some implementations, receiving coil assembly may be housed in a hermetically-sealed biocompatible housing that can be implanted in a patient's body. The transmitting and receiving resonant coils are constructed as to have closely matched or identical resonant frequencies so that the magnetic field produced by the transmitting resonant coil causes the receiving resonant coil to resonate strongly. The receiving resonant coil may resonate even when the distance between the two resonant coils greatly exceeds the greatest dimension (e.g. largest of the length, width, diameter, etc.) of either coil. In this way, the transmitting and receiving resonant coils are coupled by magnetic resonance. The power pick-up coil inductively receives energy from the magnetic field of the receiving resonant coil to provide power to an implantable medical device.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
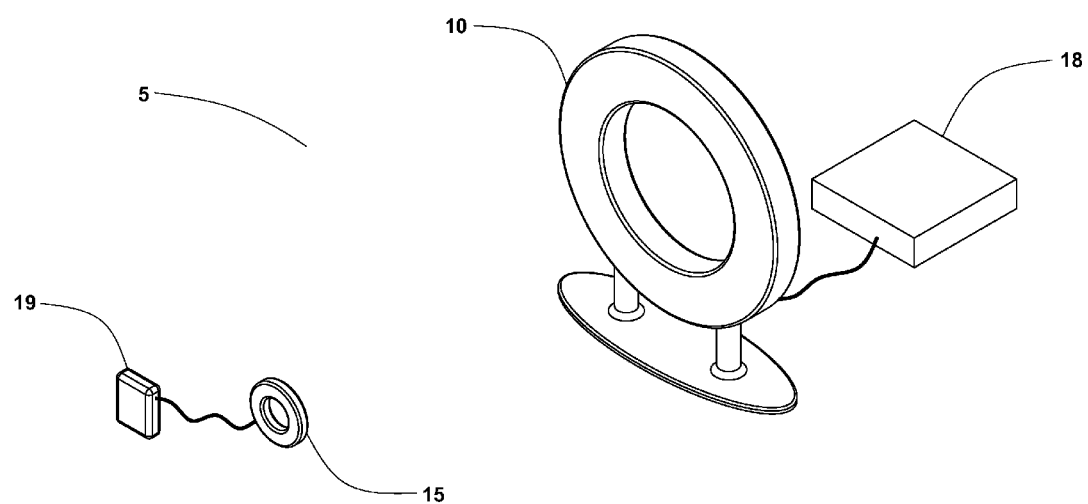
FIG. 1 is an illustrative implementation of a wireless power system.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

The following detailed description provides implantable, energy efficient, small, wireless power transfer systems and methods capable of providing power to an active implantable medical device and simultaneously recharging implantable batteries. The wireless power transfer systems and methods are capable of operating over long distances between receiving and external transmitting coil assemblies. For example, the wireless power systems and methods may be capable of transmitting power over distances ranging from a few inches to several feet. In some implementations, one or more components of the wireless power system may be implanted and the system may transmit power through the skin without percutaneous wires. In a non-limiting illustrative implementation of the wireless power system and method, the wireless power transfer system may be suitable for use with a ventricular assist device (VAD) or total artificial heart (TAH). The receiving coil assembly may be implanted in any suitable physical location in a patient's body including, but not limited to, abdominally or pectorally. Those skilled in the art will appreciate that the various features discussed below can be combined in various manners, in addition to the implementations discussed below. The illustrative implementations discussed herein are provided for illustrative purpose, and the scope of the invention is in no way limited to the specific illustrative implementations discussed herein.

Figure 2:
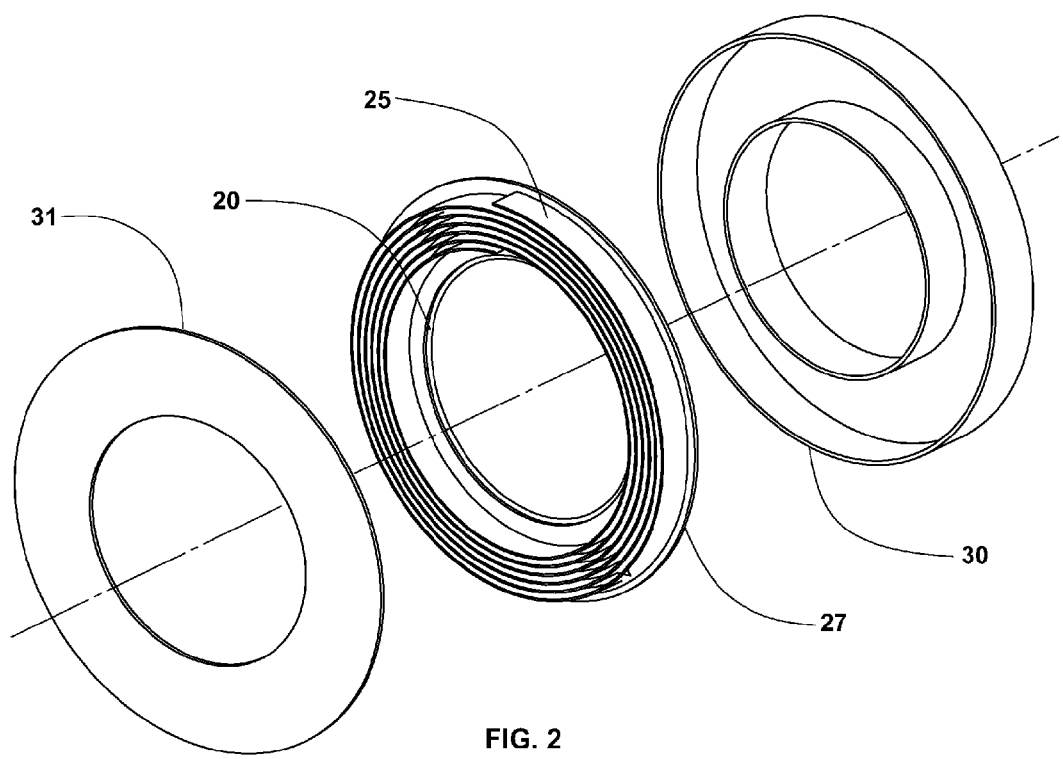
FIG. 2 is an isometric view of an illustrative implementation of a transmitting coil assembly.
Figure 3:
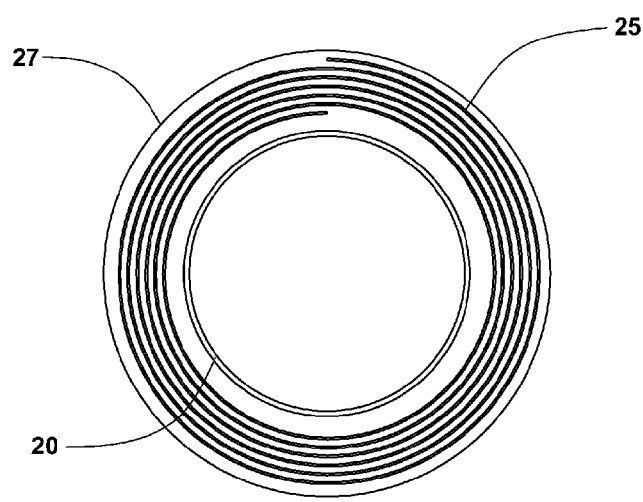
FIG. 3 is a front view of an illustrative implementation of a transmitting resonant coil and excitation coil.
Figure 4:
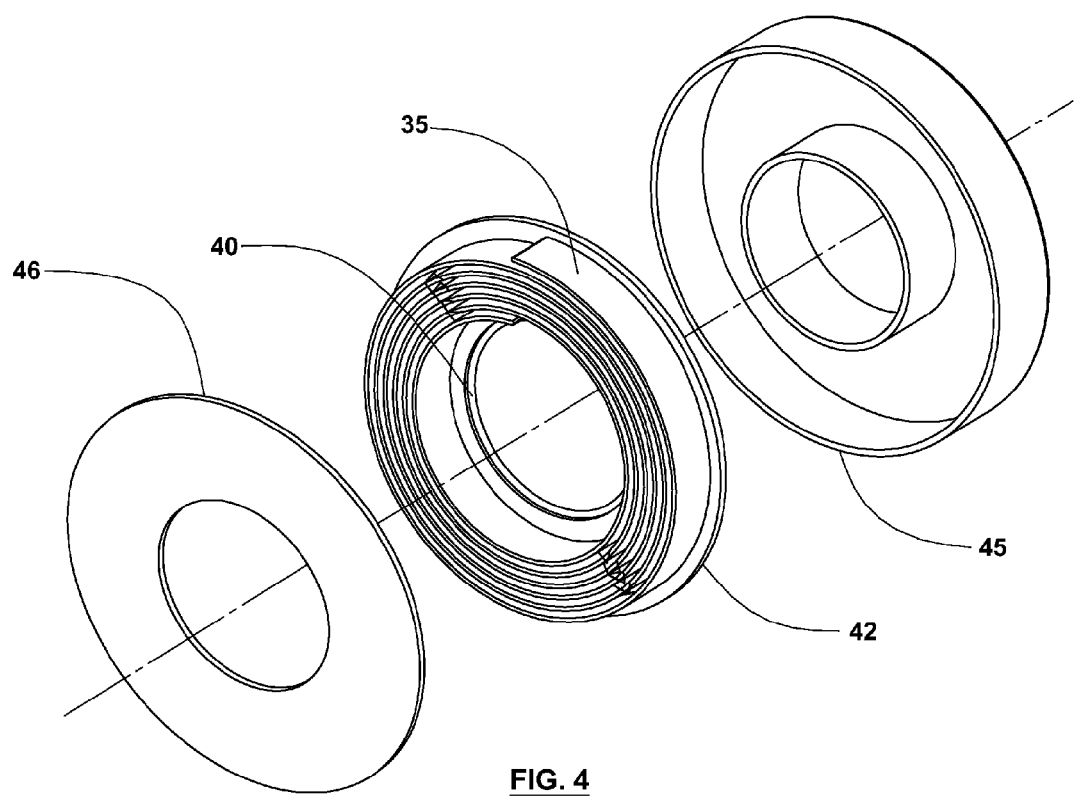
FIG. 4 is an isometric view of an illustrative implementation of a receiving coil assembly.

FIG. 1 is an isometric view of an illustrative implementation of a wireless power system 5. Wireless power system 5 may include transmitting coil assembly 10, receiving coil assembly 15, RF power supply 18, and medical device 19. In some implementations, receiving coil assembly 15 and medical device 19 may be implanted in a patient. Receiving coil assembly 15 and medical device 19 may be provided in the same or separate hermetically sealed biocompatible housing(s). FIG. 2 is an isometric view of an illustrative implementation of a transmitting coil assembly 10. Transmitting coil assembly 10 may include an excitation coil 20, transmitting resonant coil 25, mounting plate 27, housing 30, and cover 31. FIG. 3 is a front view of an illustrative implementation of transmitting resonant coil 25, excitation coil 20, and mounting plate 27. Excitation coil 20 is placed close enough to transmitting resonant coil 25 to be inductively coupled such that when high frequency AC power, such as that from an RF power supply 18 shown in FIG. 1, on the order of 30 KHz-15 MHz is supplied to excitation coil 20, this causes transmitting resonant coil 25 to resonate resulting in a local time varying magnetic field. This resonant magnetic field interacts with a resonant coil provided by receiving coil assembly 15 as shown in FIG. 4. This resonant magnetic field interaction between the transmitting resonant coil 25 and a resonant coil provided by receiving coil assembly 15 is referred to as magnetic resonance coupling.

Magnetic resonant coupling, is a phenomenon in which two resonant objects tuned to the same or similar frequency electromagnetically exchange energy strongly but interact only weakly with other non-resonant objects. For example, magnetic resonance coupling may allow energy to be transferred wirelessly between two resonant coils over significant distances, whereas inductive coupling requires the two coils to be placed close to each other.

Figure 5:
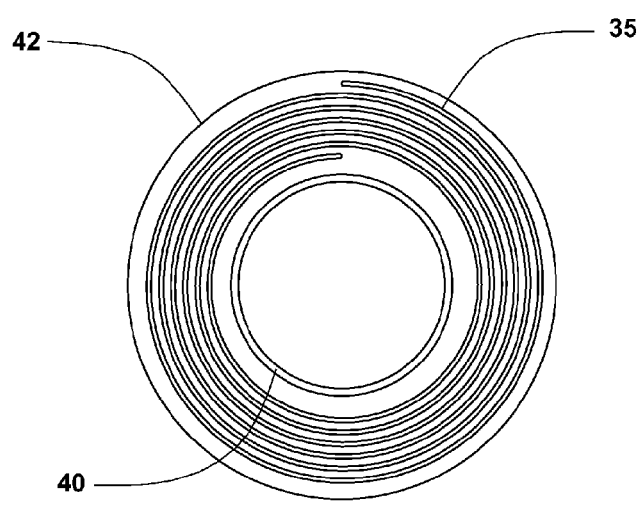
FIG. 5 is a front view of an illustrative implementation of a receiving resonant coil and power pick-up coil.

FIG. 4 is an isometric view of an illustrative implementation of a receiving coil assembly 15. Receiving coil assembly 15 provides a receiving resonant coil 35, power pick-up coil 40, mounting plate 42, hermetically-sealed biocompatible housing 45, and cover 46. FIG. 5 is a front view of an illustrative implementation of receiving resonant coil 35, power pick-up coil 40, and mounting plate 42. Excitation coil 20 and power pick-up coil 40 may be made from a minimal number of conductor loops, and with any suitable conductor material, such as stranded or solid copper wire, so as not to produce too strong inductive coupling to their respective resonant coils 25 and 35 and thereby minimize the effect on resonant coil natural frequency and Q factor as discussed further below. Housing 45 and cover 46 are made of a biocompatible material. Housing 45 and cover 46 secure and seal receiving coil assembly 15.

Transmitting resonant coil 25 and receiving resonant coil 35 are designed to have closely matched or identical natural resonant frequencies as defined by equation 1.

$$\omega = \sqrt{\frac{1}{LC}} \quad [1]$$

where, ω=coil natural resonant frequency (radians per second)

L=coil inductance (Henries)

C=coil capacitance (Farads)

By doing so, the magnetic field produced by transmitting resonant coil 25 causes receiving resonant coil 35 to strongly resonate also, generating its own local time varying magnetic field, and thereby achieves magnetic resonance coupling between the transmitting and receiving coils. In such a system, power may be transferred wirelessly and efficiently through this magnetic resonance coupling over a much greater distance than that of currently known traditional inductive coupling. Power pick-up coil 40 is placed close enough to receiving resonant coil 35 so as to receive energy from receiving resonant coil 35 inductively, causing an AC voltage across power pick-up coil 40. This AC voltage can then be rectified to a DC voltage and used to power an implantable medical device and/or recharge implantable batteries.

The amount of energy that can be transferred to receiving resonant coil 35 is proportional to the strength of magnetic field emitted from transmitting resonant coil 25. The strength of the magnetic field emitted from transmitting resonant coil 25 should be maximized for a given amount of energy input to excitation coil 20 to optimize system efficiency and power transfer as well as minimize receiving coil assembly 15 size. This is accomplished by choosing a drive frequency F that is closely matched or identical to the natural resonant frequencies ω of transmitting 25 and receiving 35 resonant coils and by increasing resonant coil quality factor Q, given by equation 2:

$$Q = \sqrt{\frac{L}{C}} * \frac{1}{R} \quad [2]$$

where, Q=coil quality factor
L=coil inductance (Henries)
C=coil capacitance (Farads)
R=coil AC resistance (Ohms) at resonant frequency ω (radians per second)

Each resonant coil should have a Q factor sufficiently high in order to provide reasonably efficient energy transfer. The diameter and placement of excitation coil 20 in relation to transmitting resonant coil 25 can be a variety of different sizes and arrangements, as the transmitting coil assembly does not have the same size and space constraints as the receiving coil assembly. In some implementations, it may be desirable to make the diameter of excitation coil 20 smaller than transmitting resonant coil 25, such that the natural resonant frequency and Q factor of transmitting resonant coil 25 is minimally affected by excitation coil 20 when placed within the enclosed volume of transmitting resonant coil 25, as shown in FIG. 3. However, in other implementations, the diameter of excitation coil 20 may be larger than transmitting resonant coil 25 and/or excitation coil 20 may be angled or out of plane with transmitting resonant coil 25 to minimize effects on the natural resonant frequency and Q factor of transmitting resonant coil 25.

One or more components of the receiving coil assembly may be implanted into a human body. Thus, it may be desirable to minimize the size of receiving resonant coil 35 and/or power pick-up coil 40 to be implanted. For example, the size of a receiving coil assembly may be minimized by placing power pick-up coil 40 within the enclosed volume of receiving resonant coil 35. The outer diameter of power pick-up coil 40 can be made smaller than the outer diameter of receiving resonant coil 35, such that the natural resonant frequency and Q factor of receiving resonant coil 35 is minimally affected by power pick-up coil 40 when placed within the enclosed volume of receiving resonant coil 35. This provides an optimum state of system tuning for maximum power transfer and efficiency while minimizing receiving coil assembly thickness and/or volume. It is important to achieve a receiving coil assembly 15 that is thin and implantable to allow for easy implantation and less noticeable implant site for patient comfort and well being. For example, in well tuned systems, receiving coil assembly 15 may be one inch or less in overall thickness. Note that in some implementations, receiving resonant coil 35 and power pick-up coil 40 may be separated so that the receiving coil assembly implanted in the patient comprises power pick-up coil 40 and not receiving resonant coil 35. Such an arrangement would minimize the size of components that are implanted in the patient, but would require receiving resonant coil 35 to be placed near the location where power pick-up coil 40 is implanted.

As can be seen in equations 1 and 2, the factors affecting the coil quality factor Q are coil inductance, capacitance, AC resistance, and resonant frequency. Specifically, to maximize Q factor, the coil inductance and resonant frequency should be maximized while the coil capacitance and AC resistance should be minimized. However, as can be seen in equation 1, coil inductance and capacitance must be chosen correctly to achieve a desired coil natural resonant frequency. For the implantable wireless power transfer system disclosed herein, the desired coil natural resonant frequency is between 30 KHz-15 MHz.

One method that can be utilized to increase coil inductance is to provide more coil turns at larger coil diameters. However, more coil turns and larger coil diameters require longer conductor lengths thereby increasing coil AC resistance and decreasing the benefit of higher inductance on coil Q factor. Furthermore, conductor lengths greater than $\frac{1}{10}^{th}$ of the resonant frequency wavelength λ may adversely impact performance due to wave reflections. Additionally, more coil turns further increase coil AC resistance because of proximity effect. Proximity effect is a well known phenomenon in which the local magnetic fields of adjacent coil turns cause current flow to be constrained to smaller and smaller conductor areas as more coil turns are added. The net effect is that a decreasing portion of available conductor area is utilized as more coil turns are added. For example, the AC resistance of a coil with 4 turns can be several times higher than a coil of the same average diameter with only 2 turns, even if the conductor length of the 4 turn coil is only twice that of the 2 turn coil.

Another phenomenon that increases coil AC resistance relative to DC resistance is the skin effect. Skin effect is caused by the internal magnetic fields generated within a single turn of conductor, as opposed to proximity effect caused by multiple conductor turns. Skin effect is similar to proximity effect in that a decreasing portion of available conductor area is utilized as AC operating frequency is increased. This results in current flow that is more concentrated at the outer surfaces of a conductor as opposed to the interior portion of a conductor. The depth to which most of the current flow is constrained in a conductor operating at a given AC frequency is known as the skin depth and is given by equation 3:

$$\delta = \sqrt{\frac{2\rho}{f\mu}} \quad [3]$$

where, δ=skin depth (meters)
ρ=resistivity of conductor (Ohm-meters)
f=operating frequency (radians per second)
μ=absolute magnetic permeability of conductor (Henries/meter)

Therefore, it can be seen for a conductor of thickness T that is much thicker than the skin depth δ, most of the conductor is not utilized to pass AC current. The ratio of conductor thickness T to skin depth δ is known as the skin depth ratio. It is clear that increasing conductor thickness T above skin depth δ does little to reduce the AC resistance of a conductor, but merely increases coil volume and mass. However, it also does not make the skin effect worse.

Notably, it is known in close coupled AC inductive transformer design that increasing conductor thickness T far above skin depth δ can worsen the proximity effect substantially, especially as more coil turns are added. For example, a high skin depth ratio above 2 can cause the AC resistance of an inductive transformer coil to be greater than 10 times higher than the same coil with a skin depth ratio of 1 or less, depending on the number of coil turns employed and operating frequency. Therefore, the conductor thickness T used in transmitting 25 and receiving 35 resonant coils is chosen to produce a skin depth ratio of less than or equal to 2 to minimize proximity effects, reduce coil AC resistance, and increase coil quality factor Q. Similarly, a skin depth ratio less than one may be advantageous. In one implementation, copper or silver foil of a thickness less than 0.020 inches is used. Counter intuitively, thin copper foil produces less AC resistance than thick copper foil for some of the operating frequencies disclosed herein. By utilizing a thin conductor, it is believed that a quality factor of 100 or greater may be achieved. In experiments using thin copper foil, a receiving resonant coil 35 with a quality factor above 300 for a coil size 3 inches or less in diameter and 0.5 inches or less in width has been achieved, which would result in a receiving coil assembly sufficiently small to implant. A receiving resonant coil 35 of the size above would then allow the entire receiving coil assembly to be less than 1 inch thick. Such a receiving resonant coil 35 may enclose an area of 7.1 in$^2$ or less. Further, the total volume of receiving resonant coil 35 may be 7.1 in$^3$ or less. Additionally, this may result in a transmitting resonant coil 25 with a quality factor above 600 for a coil size 6 inches or greater in diameter and one inch or less in width. Such a transmitting resonant coil 25 may enclose an area of 28.3 in$^2$ or more. Further, the total volume of transmitting resonant coil 25 may be 28.3 in$^3$ or more. Using the foregoing transmitting 25 and receiving 35 resonant coil diameters may result in a transmitting/receiving resonant coil diameter ratio of 2:1 or greater which may allow adequate power to be transferred over a distance equal to or greater than the diameter of receiving resonant coil 35. In experiments, we have achieved adequate power transfer over distances greater than five times the diameter of the receiving coil. Such a system design is uniquely suited for implantable wireless power systems and methods. Unlike traditional inductive coupling, such systems and methods may be capable of transmitting adequate power even when transmitting and receiving coils are laterally or angularly misaligned to a large extent, such as when a patient is sleeping.

As shown in equation 1, once the inductance of resonant coil 25 or 35 is fixed, the proper capacitance must be present for the coil to resonate at a desired frequency ω. Coil capacitance can either be intrinsic, added in the form of a fixed or variable capacitor, or both intrinsic and added. Intrinsic capacitance is that which is formed by the coil geometry itself. For example, a coil with turns made from copper or silver foil separated by one or more insulating dielectric materials such as PTFE, low-loss PTFE, polyethylene, polypropylene, vacuum, an inert gas, or air could be analogous to a flat plate capacitor of equal plate area and plate separation distance. However, intrinsic coil capacitance cannot be calculated in the same manner as a flat plate capacitor due to the effect of multiple turns. Many dielectric materials, such as those listed previously, are suitable to provide this intrinsic capacitance; however it is important that the materials have a low dielectric dissipation factor to not detrimentally impact the overall coil Q. To maintain an overall coil Q factor sufficiently high for adequate power transfer, the one or more insulating materials should have a dielectric dissipation factor of 0.01 or less at the coil resonant frequency.

It is desirable for transmitting 25 and receiving 35 resonant coils to have as little intrinsic capacitance as possible, if the intrinsic capacitance is formed partially or fully by a solid dielectric material. This is done to minimize the temperature sensitivity of the resonant coils which can shift their resonant frequencies and detune the system, resulting in lost power and efficiency. One method that can be utilized to assist in stabilizing the resonant frequency of receiving resonant coil 35 is to maintain receiving resonant coil 35 at a relatively constant temperature, such as that provided by implanting inside the human body at a temperature of 37+/−5 degrees C. Additionally, transmitting resonant coil 25 may be maintained at a relatively constant temperature of 25+/−5 degrees C. with the use of cooling fans contained in durable housing 30.

Figure 6A:
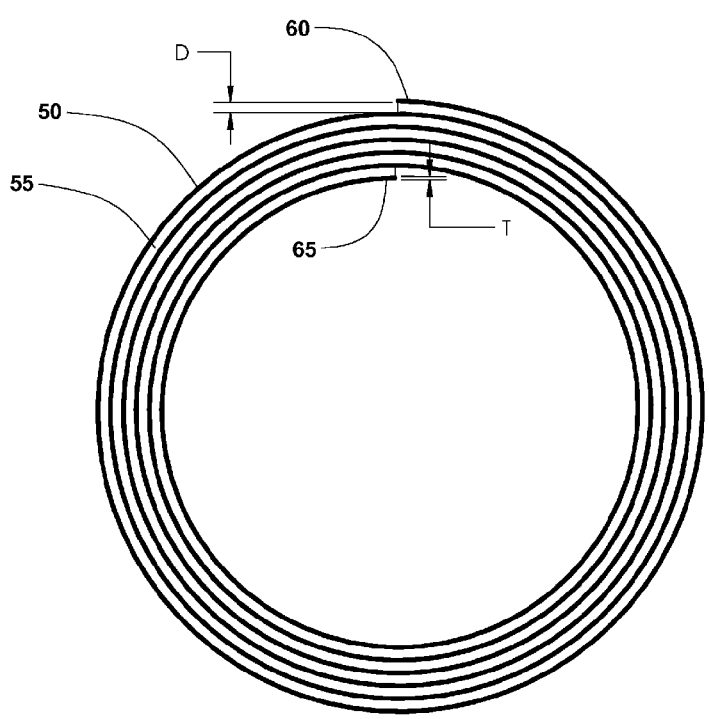
FIGS. 6a and 6b are front and side views of illustrative implementations of a resonant coil with single wrap conductive foil.
Figure 6B:
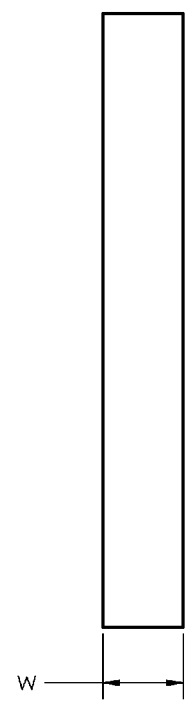

FIGS. 6a and 6b are front and side views of illustrative implementations of a resonant coil, such as transmitting or receiving resonant coil, with single wrap conductive foil. In one implementation, resonant coils 25 and 35 achieve very low intrinsic capacitance using a flat conductor geometry, such as conductive foil 50 constructed from one or more high conductivity materials such as copper or silver, separated by an insulating medium 55 composed of one or more low dielectric constant materials such as PTFE, low-loss PTFE, polyethylene, polypropylene, vacuum, an inert gas, air, or any combination thereof with relatively large spacing D between turns as shown in FIG. 6a. As described previously, the one or more insulating materials should have a dielectric dissipation factor of 0.01 or less at the coil resonant frequency to maintain an overall coil Q factor sufficiently high for adequate power transfer. Spacing D indicates the total thickness of the insulating medium 55. In some implementations, insulating medium 55 may be composed of at least one solid material with a polygonal cross section that also provides mechanical support for the conductive foil 50. A polygonal cross section, defined as a cross sectional shape with all straight sides, is chosen as it is a readily available form of PTFE, low loss PTFE, polyethylene, and polypropylene and results in a volume efficient resonant coil assembly. In the side view shown in FIG. 6b, width W may indicate the width of the conductive foil 50 and insulating medium 55. The amount of capacitance can be varied by increasing/decreasing the spacing D between coil turns or increasing/decreasing the conductor width W. Spacing D can be kept constant or varied between any adjacent turns so long as it results in the desired low intrinsic capacitance. One or more fixed or variable external capacitors with low temperature sensitivity may be added across the start and end of the coil turns to tune the coil to a desired resonant frequency. Low dielectric dissipation factor external capacitors should be used so that when combined with the insulating medium 55, the combined dielectric dissipation factor of the external capacitors and insulating medium 55 is low to maintain an overall coil Q factor sufficiently high for adequate power transfer. Low temperature sensitivity external capacitance with a temperature coefficient of less than 3000 ppm/degree C. should be used and the external capacitance should be at least one tenth the intrinsic capacitance to positively impact the thermal stability of the overall coil capacitance. The start 60 and end 65 of conductive foil 50 may be approximately within 45 degrees of each other to minimize external capacitor lead length.

In an illustrative implementation, conductive foil 50 used in resonant coils 25 and 35 is chosen with a thickness T, such that the skin depth ratio is less than 2 for a given operating resonant frequency between 30 kHz-15 MHz. This is done to decrease the coil AC resistance and thereby increase coil Q factor. To further decrease coil resistance, the conductive foil 50 may be provided on both sides of an electrically non-conductive round or rectangular spiral coil form, made from material such as ABS or polycarbonate. For example, the electrically non-conductive round or rectangular spiral coil form may be double wrapped by adhering conductive foil 50 to both the inside and outside surfaces of the coil form. This effectively provides two single layers of conductive foil 50 on opposing faces of the non-conductive form, which may have multiple benefits. First, the conductor cross section area is doubled, resulting in lower coil DC resistance and possible higher coil Q factor, with only a small increase in coil size and mass. Second, the capacitive spacing D can be formed with an all air, inert gas, or vacuum gap, making the dielectric dissipation factor low and the intrinsic capacitance of the coil very low and inherently temperature stable. This is beneficial in keeping the system tuned to a desired resonant frequency for maximum efficiency and power transfer. Conductive foil 50 may be adhered to the electrically non-conductive form with any suitable adhesive such as epoxy, urethane, silicone, or acrylic. In some implementations, conductive foil 50 may also extend over the edges of the coil form to make electrical contact between foil on the inside and outside surfaces of the coil. Alternately, if a coil form with circular cross section is used, conductive foil 50 may be wrapped around the entire circumference of the coil form to eliminate current concentrations at conductor edges.

Alternately, the conductive path of resonant coils 25 and 35 may be formed by electroplating or electroless plating of a conductive material such as copper or silver onto a suitable electrically non-conductive form. This may result in multiple advantages. First, manufacturing material and labor costs may be lower due to eliminating costs associated with adhering conductive foil to an electrically non-conductive form. Secondly, the conductive path formed by electroplating or electroless plating is continuous around the electrically non-conducting form which may further lower coil AC resistance and increase coil Q factor. The thickness of the conductive layer plated onto the electrically non-conductive form is chosen such that the skin depth ratio is less than 2 for a given operating frequency between 30 kHz-15 MHz. Again, this is done to minimize the proximity effect and lower coil AC resistance and increase coil Q factor. Electroless plating of conductive material onto an electrically non-conductive form may be preferred over electroplating to produce a more uniform conductor thickness throughout the coil geometry. The electrically non-conductive form may be made from a material that is readily platable with copper or silver such as ABS, nylon, or polycarbonate.

Another factor which determines how much power can be transferred between transmitting coil assembly 10 and receiving coil assembly 15 is the coupling coefficient between transmitting 25 and receiving 35 resonant coils. The coupling coefficient is a function of coil geometry and varies between 0 and 1. Higher coupling coefficients allow more power to be transferred between resonant coils across greater distances. Coil turns of transmitting 25 and receiving 35 resonant coils are spaced apart (distance D shown in FIG. 6a) by at least 0.003 inches, preferably 0.030 inches or greater, to increase the coupling coefficient between coils. This also has the added benefit of reducing resonant coil intrinsic capacitance.

An alternate conducting medium for resonant coils 25 and 35 for frequencies in the range 30 kHz-5 MHz is Litz wire, which is a type of cable designed to reduce the skin effect and proximity effect losses in conductors, thereby reducing the AC resistance. Litz wire consists of multiple conductors in the form of thin round wire strands, individually insulated and twisted or woven together, following one of several prescribed patterns intended to equalize the proportion of the overall length over which each strand is at the outside. Preferably, each strand has a skin depth ratio of approximately one or less for a given operating frequency between 30 kHz-5 MHz. Operation in lower frequency ranges, for example, 135 kHz, provides several advantages for use in medical implants, including, but not limited to, increased electromagnetic safety and improved performance in the presence of metallic shielding.

Because of the criticality of this wireless power system in life support applications, such as a VAD or TAH, fault-tolerance is desired. If a failure were to occur which impairs the power transfer using magnetic resonance coupling, the excitation coil and power pick-up coil 40 could be used directly as power transfer coils utilizing traditional inductive coupling over a shorter distance. For example, transmitting coil assembly 10 may be placed on the patient's body near the location of receiving coil assembly 15. To minimize the inductive coupling distance and maximize the power transfer, in some implementations it may be desirable to orient the excitation coil 20 and the power pick-up coil 40 proximate to each other with their respective transmitting and receiving resonant coils 25 and 35 being oriented distally. In other implementations, a second excitation coil separate from the transmitting coil assembly may be used to supply power inductively to the power pick-up coil 40. A suitable frequency range of operation for this inductive backup mode is 30 kHz-1 MHz, with an exemplary value being 135 kHz. While this backup mode operation is suitable for all of the previously described implementations, it is especially well suited for the Litz wire resonant coil because both the magnetic resonance coupling and the backup inductive coupling may be operated at the same frequency, simplifying system design and reducing complexity. In an alternative fault-tolerance approach, the receiving resonant coil 35 may be removed from the receiving coil assembly 15 and used as an external (non-implantable) resonator when placed in proximity to the power pick-up coil 40 in the receiving coil assembly 15. The power pick-up coil may then be used for inductive coupling as well as for collecting power from the external receiving resonant coil when magnetic resonance coupling is available.

Figure 7:
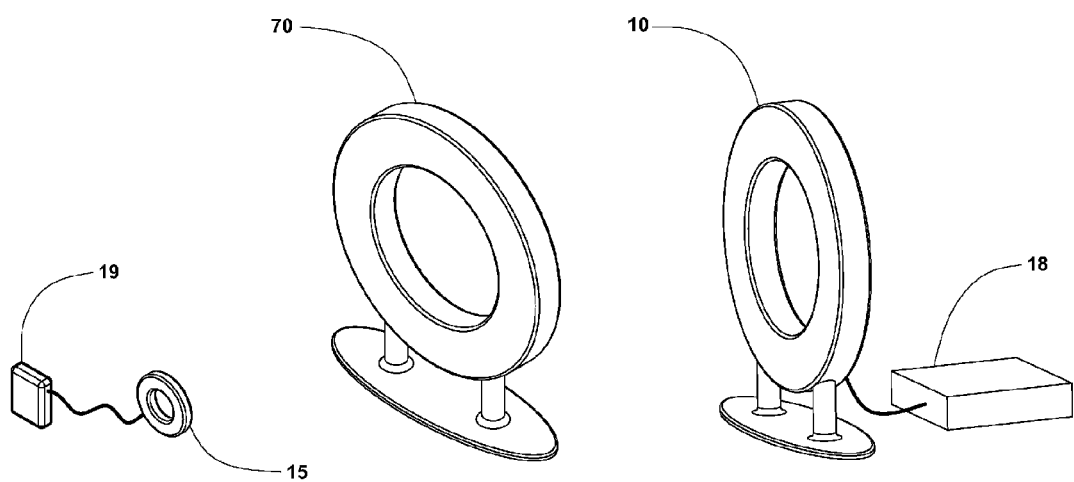
FIG. 7 is an illustrative implementation of a wireless power system with a sympathetic coil.

The power transfer efficiency of magnetic resonance coupling is increased when the Q of either or both of the resonant coils 25 and 35 is increased. Additional "sympathetic" resonant coils, meaning those which closely match or are identical to the resonant frequency of the transmitting and receiving resonant coils 25 and 35, may be used to increase the power transfer efficiency and range of the transmitting and receiving resonant coils 25 and 35. For example, one or more sympathetic resonant coils 70 may be placed near the transmitting resonant coil 25 to improve the power transfer efficiency as shown in FIG. 7. The additional coils may be placed in geometric positions that enhance the directionality or universality of the power transfer. For example, the additional coils may be placed at angle(s) relative to the transmitting resonant coil 25 that increase the spatial coverage of the implantable wireless power system. In some embodiments, additional coils may be placed near or around the receiving resonant coil 35. The sympathetic resonant coil 70 shown in FIG. 7 is illustrative only; sympathetic resonant coil 70 may be in any shape, form factor, or quantity necessary to enhance the efficiency or range of power transfer among the resonant coils 25, 35 and 70. Sympathetic resonant coil 70 should have a Q factor sufficiently high in order to provide reasonably efficient energy transfer. It may be advantageous to place one or more sympathetic resonant coils so that they, along with the transmitting resonant coil 25, are over-coupled. When a first resonant coil is placed within a critical coupling distance near another resonant coil, the resonant coils have a tendency to operate at a shared resonant frequency different from their independent natural resonant frequency, which is described as over-coupled. In contrast, when a first resonant coil is substantially distant from another resonant coil, or outside of a critical coupling distance, the resonant coils maintain operation at their respective natural resonant frequencies, which is described as under-coupled. In such a system, the transmitting resonant coil 25 and one or more sympathetic resonant coils 70 produce a magnetic resonance field which shares and stores energy. This use of sympathetic resonant coil 70 is different from a use which would transfer energy from transmitting resonant coil 25 to receiving resonant coil 35 via "repeating" or "bucket brigade" architecture wherein sympathetic resonant coil 70 is an intermediary. Instead, this over-coupled mode ensures that the sympathetic resonant coil 70 has a shared resonant frequency with transmitting resonant coil 25. When receiving resonant coil 35 is substantially distant from transmitting resonant coil 25 and sympathetic resonant coil 70, receiving resonant coil 35 may be under-coupled. Alternatively, as receiving resonant coil 35 moves substantially near either transmitting resonant coil 25 or sympathetic resonant coil 70, receiving resonant coil 35 may be over-coupled and produce a shared resonant frequency.

Figure 8:
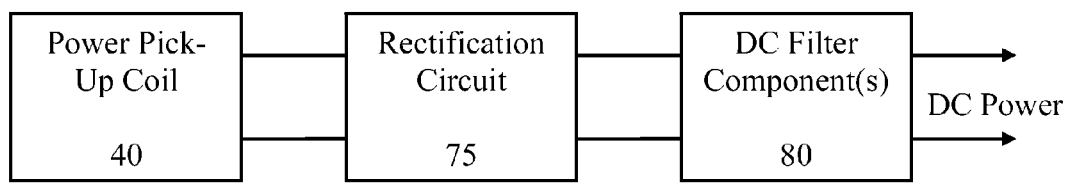
FIG. 8 is a functional block diagram of a rectifier and DC filter components connected to a power pick-up coil.

The hermetically-sealed biocompatible housing 45 and cover 46 are preferably composed of geometries and materials which do not adversely affect the Q of the receiving resonant coil 35 or the power transfer efficiency of the wireless power system. Such materials may include, but are not limited to, polyetheretherketone (PEEK), polyetherimide (ULTEM), polysulfone (UDEL), polytetraflouroethylene (PTFE, Teflon), polyurethane (Tecothane), and silicone. Additionally, the geometries and materials are chosen to provide electrical insulation for the potential high voltages that may be generated in the receiving resonant coil 35, as well as provide spacing necessary to minimize adverse impacts on the quality factor Q of receiving resonant coil 35 due to extraneous materials. Environmental capacitance, meaning capacitance in the vicinity of transmitting resonant coil 25 or receiving resonant coil 35, adversely affects the resonant frequency of coil 25 or 35 and consequently must be minimized. Therefore, the hermetically-sealed biocompatible housing 45 and cover 46 provide spacing around coil 35 and a stable electrostatic environment intended to stabilize environmental capacitance. In this way, the hermetically-sealed biocompatible housing 45 and cover 46 minimize detuning and Q reduction which would otherwise occur were housing 45 and cover 46 not designed specifically for that advantage. Sealing of biocompatible housing 45 may be accomplished with an enclosed housing or potting of an open housing using any suitable potting compound. In other implementations, sealing may be accomplished by potting the entire assembly of receiving coil assembly 15. While the hermetically-sealed biocompatible housing 45 is shown without other electronics or mechanical components common to active implantable medical devices, such as batteries, power rectification and conditioning circuitry, connectors and the like, such components may be included in or attached to housing 45. In some implementations, such components may be housed in a separate biocompatible housing. In other implementations, it may be advantageous to perform AC/DC rectification and some or all DC filtering within receiving coil assembly 15 to reduce high frequency losses which may occur in the implantable biocompatible cable connecting receiving coil assembly 15 to the implantable medical device 19. In such cases the rectifier 75 may be placed adjacent to or inside power pick-up coil 40 as shown functionally in FIG. 8. Similarly, some or all DC filter components 80, such as capacitors and inductors for a π type filter, may be placed adjacent to or inside power pick-up coil 40 also shown functionally in FIG. 8. One advantage of this approach is that the intrinsic capacitance and inductance of the implantable biocompatible cable may be leveraged as part of a π filter. All electronic components for the wireless power system can be selected for high reliability. High reliability is especially desirable for components that are to be implanted in a patient to avoid surgery to remove or repair the system. Likewise, all components of the system may be selected for compatibility with the electromagnetic fields which will be produced during the energy transfer.

The resonant coils 25 and 35 implementation previously described is a right circular spiral coil, where the start and end of the coil conductor is within 45 degrees of each other in order to reduce the effective antenna dipole and reduce electromagnetic radiation. In other implementations, any suitable coil arrangement may be utilized, such as a rectangular coil, a helical coil, a square coil, or any other suitable structure. The number of turns may be one or more. The coil may be composed of a solid conductor, hollow conductor, flat conductor, Litz wire, any other suitable conductors, and/or a combination thereof. All manner of coil shapes, including, but not limited to, circles, squares, rectangles, octagons, other polygons, regular areas and irregular areas, are within the scope of this invention. While the illustrative implementations utilize copper or silver conductor coils, any suitable conductive materials or combination of conductive materials may be utilized.

The wireless power systems and methods described herein are implantable, energy efficient, and small. The systems and methods are capable of providing power to an active implantable medical device and simultaneously recharging implantable batteries.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure.

What is claimed is the following:

1. An apparatus for use in wireless energy transfer, the apparatus comprising:
   a transmitting resonant coil providing a first conductor; and
   a receiving resonant coil, sized to be implantable in a human body, and providing a second conductor;
   wherein a first capacitor is electrically connected to the first conductor and a second capacitor is electrically connected to the second conductor; and
   wherein the first conductor and/or second conductor has a thickness T, smaller than a width W of the first conductor and/or second conductor, such that every point within the first conductor and/or second conductor resides within a skin depth at a resonant frequency of the transmitting resonant coil and/or receiving resonant coil, wherein the skin depth is defined by $$\delta = \sqrt{\frac{2\rho}{f\mu}}$$

where δ is the skin depth, ρ is a resistivity of the first conductor and/or second conductor, f is the resonant frequency, and μ is an absolute magnetic permeability of the first conductor and/or second conductor;
   wherein the thickness T is less than 0.02 inches and the width W is 0.5 inch or less; and
   wherein the transmitting and/or receiving resonant coil has a diameter of 3 inches or less.

2. The apparatus of claim 1, wherein the first conductor and/or second conductor is a foil or a plating.

3. The apparatus of claim 1, wherein the first conductor and/or second conductor provides two conductive layers arranged on opposing faces of a coil structure formed from an electrically non-conductive material.

4. The apparatus of claim 1, wherein the first conductor and/or second conductor provides a continuous electrically conductive layer arranged around all surfaces of a coil structure formed from an electrically non-conductive material.

5. The apparatus of claim 1, wherein an enclosed area of the transmitting resonant coil is at least twice an enclosed area of the receiving resonant coil.

6. The apparatus of claim 1, wherein the receiving resonant coil is secured in a hermetically-sealed biocompatible housing, and the receiving resonant coil is implantable into a human body.

7. The apparatus of claim 1, wherein a distance between the transmitting resonant coil and the receiving resonant coil is equal to or greater than five times a largest dimension of the receiving resonant coil.

8. The apparatus of claim 1, wherein the receiving resonant coil provides power to recharge an implantable battery, to operate an implantable medical device, or to simultaneously recharge an implantable battery and operate an implantable medical device.

9. The apparatus of claim 1 comprising one or more sympathetic resonant coils, wherein the sympathetic resonant coils extend a transmission range for wireless energy transfer.

10. The apparatus of claim 9, wherein one or more sympathetic resonant coils are over-coupled with the transmitting resonant coil.

11. The apparatus of claim 1, wherein a first electrical insulating medium between coil turns of the transmitting resonant coil and/or a second electrical insulating medium between coil turns of the receiving resonant coil provides a dielectric dissipation factor of 0.01 or less.

12. The apparatus of claim 1, wherein a first electrical insulating medium between coil turns of the transmitting resonant coil and/or a second electrical insulating medium between coil turns of the receiving resonant coil is solid with a polygonal cross section.

13. The apparatus of claim 1, wherein the transmitting and/or receiving resonant coil has a quality factor Q greater than 100.

14. The apparatus of claim 1, wherein the transmitting and/or receiving resonant coil has a quality factor Q greater than 300.

15. The apparatus of claim 1, wherein an electrical insulating medium between coil turns of the receiving resonant coil provides a dielectric dissipation factor of 0.01 or less;
   wherein the second conductor is a foil or a plating;
   wherein the insulating medium is solid with a polygonal cross section; and
   wherein the receiving resonant coil has a quality factor Q greater than 300.

16. The apparatus of claim 1, wherein the transmitting resonant coil has a diameter of 6 inches or greater.

17. The apparatus of claim 1, wherein the transmitting resonant coil has a quality factor Q greater than 600.

18. The apparatus of claim 1, wherein the first conductor has a width W of 1.0 inch or less.

19. An apparatus for use in wireless energy transfer, the apparatus comprising:
   a transmitting resonant coil providing a first conductor and a first electrical insulating medium between coil turns of the first conductor; and
   a receiving resonant coil providing a second conductor and a second electrical insulating medium between coil turns of the second conductor;
   wherein a first capacitor is electrically connected to the first conductor and a second capacitor is electrically connected to the second conductor;
   wherein the first and/or second insulating medium comprises one or more dielectric materials that is solid with a polygonal cross section, the first and/or second insulating medium providing a dielectric dissipation factor of 0.01 or less;
   wherein the first and/or second conductor has a thickness T of less than 0.02 inches and a width W of 0.5 inch or less; and
   wherein the transmitting and/or receiving resonant coil has a diameter of 3 inches or less.

20. The apparatus of claim 19, wherein the first and/or second conductor has an inter-turn spacing D greater than 0.003 inch.

21. The apparatus of claim 19, wherein each of the first and second capacitors has a temperature coefficient of less than 3000 ppm/degree C. and a total capacitance at least one tenth of the capacitance provided by the first and/or second insulating medium.

22. The apparatus of claim 19, wherein the first capacitor is electrically connected to a start and an end of the coil turns of the first conductor, the second capacitor is electrically connected to a start and an end of the coil turns of the second conductor, and each of the first and second capacitors has a dielectric dissipation factor of 0.01 or less.

23. The apparatus of claim 19, wherein the thickness T and the width W are sized such that every point within the first conductor and/or second conductor resides within a skin depth at a resonant frequency of the transmitting resonant coil and/or receiving resonant coil, wherein the skin depth is defined by $$\delta = \sqrt{\frac{2\rho}{f\mu}}$$

where δ is the skin depth, ρ is a resistivity of the first conductor and/or second conductor, f is the resonant frequency, and μ is an absolute magnetic permeability of the first conductor and/or second conductor.

24. The apparatus of claim 19, wherein the thickness T is smaller than the width W and wherein the first conductor and/or second conductor is a foil or a plating.

25. The apparatus of claim 19, wherein the transmitting and/or receiving resonant coil has a quality factor Q greater than 100.

26. The apparatus of claim 19, wherein the transmitting and/or receiving resonant coil has a quality factor Q greater than 300.

27. The apparatus of claim 19, wherein the thickness T is smaller than the width W, such that every point within the second conductor resides within a skin depth at a resonant frequency of the receiving resonant coil, wherein the skin depth is defined by $$\delta = \sqrt{\frac{2\rho}{f\mu}}$$

where δ is the skin depth, ρ is a resistivity of the second conductor, f is the resonant frequency, and μ is an absolute magnetic permeability of the second conductor;
   wherein the second conductor is a foil or a plating;
   wherein the second insulating medium has a polygonal cross section; and
   wherein the receiving resonant coil has a quality factor Q greater than 300.

28. The apparatus of claim 19, wherein the transmitting resonant coil has a diameter of 6 inches or greater.

29. The apparatus of claim 19, wherein the transmitting resonant coil has a quality factor Q greater than 600.

30. The apparatus of claim 19, wherein the first conductor has a width W of 1.0 inch or less.

31. An apparatus for use in wireless energy transfer, the apparatus comprising:
   a transmitting resonant coil providing a first conductor and a first electrical insulating medium between coil turns of the first conductor;
   a receiving resonant coil providing a second conductor and a second electrical insulating medium between coil turns of the second conductor; and
   a biocompatible housing which houses and hermetically seals the receiving resonant coil, a rectification circuit, and DC filter components from body fluids and tissues;
   wherein a first capacitor is electrically connected to the first conductor and a second capacitor is electrically connected to the second conductor;
   wherein the first and/or second insulating medium comprises one or more solid dielectric materials providing a dielectric dissipation factor of 0.01 or less;
   wherein the first and/or second conductor has a thickness T of less than 0.02 inches and a width W of 0.5 inch or less;
   wherein the thickness T is smaller than the width W; and
   wherein the transmitting and/or receiving resonant coil has a diameter of 3 inches or less.

32. The apparatus of claim 31, wherein the thickness T and the width W are sized such that every point within the first conductor and/or second conductor resides within a skin depth at a resonant frequency of the transmitting resonant coil and/or receiving resonant coil, wherein the skin depth is defined by $$\delta = \sqrt{\frac{2\rho}{f\mu}}$$

where δ is the skin depth, ρ is a resistivity of the first conductor and/or second conductor, f is the resonant frequency, and μ is an absolute magnetic permeability of the first conductor and/or second conductor.

33. The apparatus of claim 31, wherein the first conductor and/or second conductor is a foil or a plating.

34. The apparatus of claim 31, wherein the first and/or second insulating medium has a polygonal cross section.

35. The apparatus of claim 31, wherein the transmitting and/or receiving resonant coil has a quality factor Q greater than 100.

36. The apparatus of claim 31, wherein the transmitting and/or receiving resonant coil has a quality factor Q greater than 300.

37. The apparatus of claim 31, wherein the thickness T is smaller than the width W, such that every point within the second conductor resides within a skin depth at a resonant frequency of the receiving resonant coil, wherein the skin depth is defined by $$\delta = \sqrt{\frac{2\rho}{f\mu}}$$

where δ is the skin depth, ρ is a resistivity of the second conductor, f is the resonant frequency, and μ is an absolute magnetic permeability of the second conductor;
   wherein the second conductor is a foil or a plating;
   wherein the second insulating medium has a polygonal cross section; and
   wherein the receiving resonant coil has a quality factor Q greater than 300.

38. The apparatus of claim 31, wherein the transmitting resonant coil has a diameter of 6 inches or greater.

39. The apparatus of claim 31, wherein the transmitting resonant coil has a quality factor Q greater than 600.

40. The apparatus of claim 31, wherein the first conductor has a width W of 1.0 inch or less.

41. An apparatus for use in wireless energy transfer, the apparatus comprising:
   a transmitting resonant coil providing a first conductor; and
   a receiving resonant coil being hermetically sealed in a biocompatible housing sized to be implantable inside a human body, wherein the receiving resonant coil comprises a second conductor;
   wherein a first capacitor is electrically connected to the first conductor and a second capacitor is electrically connected to the second conductor;
   wherein the first conductor and/or second conductor has a thickness T, smaller than a width W of the first conductor and/or second conductor, such that every point within the first conductor and/or second conductor resides within a skin depth at a resonant frequency of the transmitting resonant coil and/or receiving resonant coil, wherein the skin depth is defined by $$\delta = \sqrt{\frac{2\rho}{f\mu}}$$

where δ is the skin depth, ρ is a resistivity of the first conductor and/or second conductor, f is the resonant frequency, and μ is an absolute magnetic permeability of the first conductor and/or second conductor;

wherein the thickness T is less than 0.02 inches and the width W is 0.5 inch or less; and wherein the transmitting and/or receiving resonant coil has a diameter of 3 inches or less.

42. The apparatus of claim 41, wherein a first electrical insulating medium between coil turns of the transmitting resonant coil and/or a second electrical insulating medium between coil turns of the receiving resonant coil provides a dielectric dissipation factor of 0.01 or less.

43. The apparatus of claim 41, wherein a first electrical insulating medium between coil turns of the transmitting resonant coil and/or a second electrical insulating medium between coil turns of the receiving resonant coil is solid with a polygonal cross section.

44. The apparatus of claim 41, wherein the transmitting and/or receiving resonant coil has a quality factor Q greater than 100.

45. The apparatus of claim 41, wherein the transmitting and/or receiving resonant coil has a quality factor Q greater than 300.

46. The apparatus of claim 41, wherein an electrical insulating medium between coil turns of the receiving resonant coil provides a dielectric dissipation factor of 0.01 or less;

wherein the second conductor is a foil or a plating; and
wherein the receiving resonant coil has a quality factor Q greater than 300.

47. The apparatus of claim 41, wherein the transmitting resonant coil has a diameter of 6 inches or greater.

48. The apparatus of claim 41, wherein the transmitting resonant coil has a quality factor Q greater than 600.

49. The apparatus of claim 41, wherein the first conductor has a width W of 1.0 inch or less.

* * * * *